US012484988B2

(12) United States Patent
Kirschman et al.

(10) Patent No.: US 12,484,988 B2
(45) Date of Patent: Dec. 2, 2025

(54) SURGICAL INSTRUMENT WRAP UTILIZING DIFFUSIBLE FLUORESCENT LAYER

(71) Applicants: David Louis Kirschman, Dayton, OH (US); Javad Parvizi, Gladwyne, PA (US); Peter Sharkey, Villanova, PA (US)

(72) Inventors: David Louis Kirschman, Dayton, OH (US); Javad Parvizi, Gladwyne, PA (US); Peter Sharkey, Villanova, PA (US)

(73) Assignee: Sterintact LLC, Dayton, OH (US)

( * ) Notice: Subject to any disclaimer, the term of this patent is extended or adjusted under 35 U.S.C. 154(b) by 487 days.

(21) Appl. No.: 18/161,375

(22) Filed: Jan. 30, 2023

(65) Prior Publication Data

US 2023/0285102 A1 Sep. 14, 2023

Related U.S. Application Data

(60) Provisional application No. 63/318,608, filed on Mar. 10, 2022.

(51) Int. Cl.
*A61B 46/10* (2016.01)
*A61B 46/00* (2016.01)
*A61B 50/33* (2016.01)
*A61L 2/28* (2006.01)

(52) U.S. Cl.
CPC .............. *A61B 46/10* (2016.02); *A61B 46/40* (2016.02); *A61B 50/33* (2016.02); *A61L 2/28* (2013.01)

(58) Field of Classification Search
CPC ......... A61B 46/10; A61B 46/40; A61B 50/33; A61B 50/30; A61L 2/28; A61L 2/04; A61L 2/07; A61L 2202/122; A61L 2202/24
See application file for complete search history.

(56) References Cited

U.S. PATENT DOCUMENTS

| | | | |
|---|---|---|---|
| 3,674,648 | A | 7/1972 | Soli |
| 4,444,185 | A | 4/1984 | Shugar |
| 4,620,845 | A | 11/1986 | Popovich et al. |
| 4,882,496 | A | 11/1989 | Bellotti et al. |
| 5,005,573 | A | 4/1991 | Buchanan |

(Continued)

FOREIGN PATENT DOCUMENTS

| | | | |
|---|---|---|---|
| WO | 02065972 A2 | 8/2002 |
| WO | WO 02/065972 | 8/2002 |
| WO | 2012108907 A1 | 8/2012 |

*Primary Examiner* — Michael C Miggins
(74) *Attorney, Agent, or Firm* — Jacox, Meckstroth & Jenkins

(57) ABSTRACT

A surgical instrument wrap having at least one or a plurality of fibrous layers that cooperate with at least one agent or dye layer that is generally not visible until the at least one or plurality of fibrous layers is damaged or disrupted. The at least one diffusible agent or dye layer diffuses or wicks into the disrupted or damaged area. A fluorescent dye, a reactive dye, a conjugant dye or an absorption wavelength of approximately 200-400 nanometers in one embodiment and an emission wavelength in the visible spectrum so that when the surgical wrap is damage or disrupted and then exposed to, for example, a fluorescent or ultraviolet light source, the agent or dye fluoresces to provide an indication to the user that damage to the wrap has occurred. The user can presume that the items or instruments in the surgical tray may be contaminated.

51 Claims, 7 Drawing Sheets

(56) References Cited

U.S. PATENT DOCUMENTS

| | | | |
|---|---|---|---|
| 5,116,317 | A | 5/1992 | Carson, Jr. et al. |
| 5,165,395 | A | 11/1992 | Ricci |
| 5,193,544 | A | 3/1993 | Jaffe |
| 5,240,675 | A | 8/1993 | Wilk et al. |
| 5,260,020 | A | 11/1993 | Wilk et al. |
| 5,522,868 | A | 6/1996 | Buckley et al. |
| 5,637,877 | A | 6/1997 | Sinofsky |
| 5,695,482 | A | 12/1997 | Kaldany |
| 5,855,203 | A | 1/1999 | Matter |
| 5,891,082 | A | 4/1999 | Leone et al. |
| 6,443,147 | B1 | 9/2002 | Matter |
| 6,470,888 | B1 | 10/2002 | Matter |
| 10,029,841 | B2 | 7/2018 | Gaines et al. |
| 10,139,389 | B2 | 11/2018 | Moore et al. |
| 2001/0047195 | A1 | 11/2001 | Crossley |
| 2002/0074559 | A1 | 6/2002 | Dowling et al. |
| 2002/0165594 | A1 | 11/2002 | Biel |
| 2003/0017073 | A1 | 1/2003 | Eckhardt et al. |
| 2003/0114842 | A1 | 6/2003 | DiStefano |
| 2004/0158302 | A1 | 8/2004 | Chornenky et al. |
| 2005/0279354 | A1 | 12/2005 | Deutsch et al. |
| 2006/0130846 | A1 | 6/2006 | Rife |
| 2007/0128094 | A1 | 6/2007 | Paris-Jolly et al. |
| 2007/0176117 | A1 | 8/2007 | Redmond et al. |
| 2007/0187626 | A1 | 8/2007 | Gaska et al. |
| 2008/0159908 | A1 | 7/2008 | Redmond |
| 2008/0306454 | A1 | 12/2008 | Sikora |
| 2009/0257910 | A1 | 10/2009 | Segal |
| 2010/0264329 | A1 | 10/2010 | Vardiel et al. |
| 2010/0324505 | A1 | 12/2010 | Levenson et al. |
| 2011/0287553 | A1 | 11/2011 | Hassan et al. |
| 2012/0116294 | A1 | 5/2012 | Boenig et al. |
| 2013/0303996 | A1 | 11/2013 | Rasooly et al. |
| 2014/0039418 | A1 | 2/2014 | Rioux et al. |
| 2015/0126976 | A1 | 5/2015 | Tang et al. |
| 2016/0137381 | A1 | 5/2016 | Gaines et al. |
| 2017/0168037 | A1 | 6/2017 | Moore et al. |
| 2018/0297765 | A1 | 10/2018 | Gaines et al. |

SURGICAL INSTRUMENT WRAP UTILIZING DIFFUSIBLE FLUORESCENT LAYER

CROSS-REFERENCE TO RELATED APPLICATION

The present application claims priority to provisional U.S. Application Ser. No. 63/318,608 filed Mar. 10, 2022, to which Applicant claims the benefit of the filing date of this provisional application, which is incorporated herein by reference and made a part hereof.

BACKGROUND OF THE INVENTION

1. Field of the Invention

This application relates to a surgical instrument wrap having at least one or a plurality of fibrous layers that cooperate with at least one agent or dye layer that is generally not visible until damage or disruption of the at least one or plurality of fibrous layers has occurred.

2. Description of the Related Art

Sterile wrapping in the operating room (OR) is essential to preserving the sterility of equipment in surgical procedures. Surgical instrument trays are wrapped in double-layered textile wraps and placed in a steam sterilizer. The wraps transmit steam and heat into the tray to allow for sterilization to occur. Post sterilization wrapped trays are transported to the OR and unwrapped for use in the surgical procedure. However, wraps are prone to damage in the form of tearing and puncture during storage and handling. These defects can allow bacteria and other contaminants to access the internal instrumentation, leading to dangerous and costly surgical site infections. As part of routine preoperative practice in the United States, surgical staff visually inspect wraps for damage, but often fail to detect small holes or tears.

What is needed, therefore, is a damage detector or damage indication means for surgical wraps in the form of a heat-resistant and gas permeable fluorescent layer, which will not discolor surgical instrumentation, and which will be detectible under certain light wavelengths for operating room inspection.

SUMMARY OF THE INVENTION

One object of the invention is to provide a surgical instrument wrap utilizing a diffusible fluorescent layer.

Another object of the invention is to provide a surgical instrument wrap having a damage detection or indication device or means to provide an indication when the wrap has been damaged or disrupted.

Another object of the invention is to provide a surgical instrument wrap having damage indication means and that is heat resistant and that permits gas, steam or fluid sterilization or irradiation and gas, steam or fluid permeability into the wrap and to the items or instruments therein.

Another object of the invention is to provide an apparatus and means for detecting when a surgical wrap has been damaged, thereby increasing the probability that items or instruments in the surgical tray may be contaminated.

Another object of the invention is to provide a surgical instrument wrap having a diffusible dye or agent layer that is gas, steam or fluid permeable and/or capable of irradiation.

Still another object of the invention is to provide a surgical instrument wrap having at least one fibrous layer and at least one diffusible agent or dye layer that is gas permeable but will not discolor the items or surgical instrumentation in the surgical tray.

In one aspect, one embodiment of the invention comprises a surgical tray damage protection system for use with a surgical instrument tray having at least one surgical instrument, the damage protection system comprising at least one fibrous layer comprising a predetermined arrangement of fibers; and at least one diffusible agent layer comprising a diffusible agent which fluoresces when exposed to a light having a predetermined light wavelength; the at least one fibrous layer and the at least one diffusible agent layer being arranged on the surgical instrument tray such that upon a disruption or damage to at least one fiber of the at least one fibrous layer, at least a portion of the at least one diffusible agent layer diffuses into the disrupted or damaged at least one fiber so that at least a portion of the disrupted or damaged at least fiber becomes colored, stained or dyed by the at least a portion of the at least one diffusible agent layer; the at least a portion of the disrupted or damage at least one fiber having the agent fluorescing when exposed to light of a predetermined wavelength.

In another aspect, another embodiment of the invention comprises a container having a damage indication wrap at least partially covering the container, the container being adapted to house at least one item thereon, the container comprising a container body having an area therein for receiving the at least one item; the damage indication wrap comprising at least one fibrous layer comprising a predetermined arrangement of fibers; and at least one diffusible agent layer comprising a diffusible agent which fluoresces when exposed to a light having a predetermined light wavelength; the at least one fibrous layer and the at least one diffusible agent layer being arranged on the container such that upon a disruption or damage to at least one fiber of the at least one fibrous layer, at least a portion of the at least one diffusible agent layer diffuses into the disrupted or damaged at least one fiber so that at least a portion of the disrupted or damaged at least fiber becomes colored, stained or dyed by the at least a portion of the at least one diffusible agent layer; the at least a portion of the disrupted or damaged at least one fiber having the agent fluorescing when exposed to light of a predetermined wavelength.

In still another aspect, another embodiment of the invention comprises a surgical wrap comprising of at least one fibrous barrier layer comprising a structure of cellulosic fibers; a diffusible dye layer comprising a diffusible dye which fluoresces when exposed to a specific light wavelength; the barrier layer and the dye layer disposed such that disruption of the fibers results in selective diffusion of the dye into the disrupted fiber edges; the disrupted fiber edges fluorescing when exposed to the light wavelength.

In still another aspect, another embodiment of the invention comprises a surgical wrap damage detection system comprising a barrier layer comprising a structure of fibrous construction; a diffusible dye layer which fluoresces when exposed to a specific light wavelength; the barrier layer and the dye layer disposed such that disruption of the fibers results in selective diffusion of the dye into the disrupted fiber edges; a light source emitting a wavelength equivalent to the absorption wavelength of the dye layer.

In yet another aspect, another embodiment of the invention comprises a method for locating damage to a surgical wrap comprising the steps of wrapping a surgical instrument or container with barrier layer comprising a structure of fibrous construction; the wrap further comprising a diffusible dye layer which fluoresces when exposed to a specific light wavelength; utilizing a light source with an ultraviolet, visual, infrared or electromagnetic wavelength adapted to illuminate the barrier layer; visualizing fluorescent emission from disrupted and absorptive fiber edges resulting from diffusion of the dye layer into the barrier layer; the fluorescent emission localized to disrupted fiber edges resulting in circumferential fluorescence about the damage.

This invention, including all embodiments shown and described herein, could be used alone or together and/or in combination with one or more of the features covered by one or more of the following list of features which may be combined, used independently or the like:

The surgical tray damage protection system wherein the at least one fibrous layer comprises a plurality of cellulose fibers.

The surgical tray damage protection system wherein the agent comprises at least one of a fluorescent dye, a reactive dye, a conjugated dye or a protein.

The surgical tray damage protection system wherein the agent comprises an absorption wavelength of 300-400 nanometers and an emission wavelength in the visible spectrum.

The surgical tray damage protection system wherein the agent comprises an absorption wavelength of 200-400 nanometers and an emission wavelength in the visible spectrum.

The surgical tray damage protection system wherein the agent comprises an absorption wavelength of 10-400 nanometers and an emission wavelength in the visible spectrum.

The surgical tray damage protection system wherein the disruption or damage to at least one fiber of the at least one fibrous layer comprises a plurality of damaged fibers that are torn, cut, ripped, shredded, damaged or the like that disrupts the integrity or constitution of the plurality of fibers in the fibrous layer, at least a portion of the plurality of damaged fibers becoming colored, stained or dyed by the at least a portion of the at least one diffusible agent layer which diffuses into the disrupted, torn, ripped, shredded or damaged areas of the plurality of fibers.

The surgical tray damage protection system wherein the agent comprises at least one of a fluorescent dye, a reactive dye, a conjugated dye or a protein, the damage to the at least one fiber comprises a damaged to the at least one fibrous layer comprising a plurality of torn edges of the fibers that absorb the agent.

The surgical tray damage protection system wherein the at least one fibrous layer overlays a majority of the at least one diffusible agent so that the agent is not visible until at least one fiber of the at least one fibrous layer is damaged or disrupted.

The surgical tray damage protection system wherein after the at least one diffusible agent diffuses into the damaged or disrupted plurality of fibers, the diffusible agent does not fluoresce and is not detectible to the naked eye until exposed to the predetermined light wavelength.

The surgical tray damage protection system wherein the diffusible agent comprises a diffusible dye that is a fluid having a predetermined viscosity and flow rate.

The surgical tray damage protection system wherein at least one fibrous layer is at least one of gas permeable or heat resistant so that instruments in the surgical tray may be sterilized after the at least one fibrous layer and the diffusible agent layer are situated on the surgical tray, with the layers remaining substantially intact.

The surgical tray damage protection system wherein at least one fibrous layer comprises a plurality of cellulose fibers comprising at least one of a non-porous or closed-cell conformation that converts to a porous or open-cell conformation upon the disruption or damage to facilitate diffusion of the agent into the damage or disrupted portion of the at least one fiber.

The surgical tray damage protection system wherein the at least one fibrous layer, upon mechanical disruption increases one or more of fiber surface area, fiber porosity or fiber open-cell conformation, resulting in increased diffusion gradient between the disrupted fibers and the diffusible agent.

The surgical tray damage protection system where the diffusible agent comprises one or more reactive dyes, conjugated dyes and/or proteins with an absorption wavelength of 300-400 nanometers, and an emission wavelength in the visible spectrum.

The surgical tray damage protection system where the diffusible agent comprises one or more reactive dyes, conjugated dyes and/or proteins with an absorption wavelength of 200-400 nanometers, and an emission wavelength in the visible spectrum.

The surgical tray damage protection system where the diffusible agent comprises one or more reactive dyes, conjugated dyes and/or proteins with an absorption wavelength of 10-400 nanometers, and an emission wavelength in the visible spectrum.

The surgical tray damage protection system wherein the at least one fibrous layer remains substantially impervious, when intact, to penetration from the diffusible agent in conditions of heat in excess of 100 degrees C. and relative humidity greater than 50%.

The surgical tray damage protection system wherein the diffusible agent imported into the surface of the at least one fibrous layer or comprising a discrete layer; the discrete layer comprising a polymer, textile, fibrous, hydrogel, membrane, matrix, or similar layer to allow for localization, retention, and outward diffusion of the dye.

The container having a damage indication wrap wherein the container is a surgical tray and the at least one item is a surgical instrument.

The container having a damage indication wrap wherein the at least one fibrous layer comprises a plurality of cellulose fibers.

The container having a damage indication wrap wherein the agent comprises at least one of a fluorescent dye, a reactive dye, a conjugated dye or a protein.

The container having a damage indication wrap wherein the agent comprises an absorption wavelength of 300-400 nanometers and an emission wavelength in the visible spectrum.

The container having a damage indication wrap wherein the agent comprises an absorption wavelength of 200-400 nanometers and an emission wavelength in the visible spectrum.

The container having a damage indication wrap wherein the agent comprises an absorption wavelength of 10-400 nanometers and an emission wavelength in the visible spectrum.

The container having a damage indication wrap wherein the disruption or damage to at least one fiber of the at least one fibrous layer comprises a plurality of damaged fibers that are torn, cut, ripped, shredded, damaged or the like that disrupts the integrity or constitution of the plurality of fibers in the fibrous layer, at least a portion of the plurality of damaged fibers becoming colored, stained or dyed by the at least a portion of the at least one diffusible agent layer which diffuses into the disrupted, torn, ripped, shredded or damaged areas of the plurality of fibers.

The container having a damage indication wrap wherein the agent comprises at least one of a fluorescent dye, a reactive dye, a conjugated dye or a protein, the damage to the at least one fiber comprises a damaged to the at least one fibrous layer comprising a plurality of torn edges of the fibers that absorb the agent.

The container having a damage indication wrap wherein the at least one fibrous layer overlays a majority of the at least one diffusible agent so that the agent is not visible until at least one fiber of the at least one fibrous layer is damaged or disrupted.

The container having a damage indication wrap wherein after the at least one diffusible agent diffuses into the damaged or disrupted plurality of fibers, the diffusible agent does not fluoresce and is not detectible to the naked eye until exposed to the predetermined light wavelength.

The container having a damage indication wrap wherein the diffusible agent comprises a diffusible dye that is a fluid having a predetermined viscosity and flow rate.

The container having a damage indication wrap wherein at least one fibrous layer is at least one of gas permeable or heat resistant so that instruments in the container may be sterilized after the at least one fibrous layer and the diffusible agent layer are situated on the container, with the layers remaining substantially intact.

The container having a damage indication wrap wherein at least one fibrous layer comprises a plurality of cellulose fibers comprising at least one of a non-porous or closed-cell conformation that converts to a porous or open-cell conformation upon the disruption or damage to facilitate diffusion of the agent into the damage or disrupted portion of the at least one fiber.

The surgical wrap wherein the cellulosic fibers, upon mechanical disruption increases one or more of fiber surface area, fiber porosity or fiber open-cell conformation, resulting in increased diffusion gradient between the disrupted fibers and the fluorescent dye.

The surgical wrap where the fluorescent dye comprises one or more reactive dyes, conjugated dyes and/or proteins with an absorption wavelength of 300-400 nanometers, and an emission wavelength in the visible spectrum.

The surgical wrap where the fluorescent dye comprises one or more reactive dyes, conjugated dyes and/or proteins with an absorption wavelength of 200-400 nanometers, and an emission wavelength in the visible spectrum.

The surgical wrap where the fluorescent dye comprises one or more reactive dyes, conjugated dyes and/or proteins with an absorption wavelength of 10-400 nanometers, and an emission wavelength in the visible spectrum.

The surgical wrap wherein the cellulosic fibers remain substantially impervious, when intact, to penetration from the fluorescent dye in conditions of heat in excess of 100 degrees C. and relative humidity greater than 50%.

The surgical wrap wherein the cellulosic fibers comprising a nonporous and/or closed-cell conformation, converting to porous and or open-cell conformation upon the event of mechanical disruption.

The surgical wrap wherein the fluorescent dye imported into the surface of the fibrous barrier layer or comprising a discrete layer, the discrete layer comprising a polymer, textile, fibrous, hydrogel, membrane, matrix, or similar layer to allow for localization, retention, and outward diffusion of the dye.

The surgical wrap damage detection system wherein the light source comprising a wavelength emission in substantially the UV-A or UV-B range, from 300-400 nanometers.

The surgical wrap damage detection system wherein the light source comprising a wavelength emission in substantially the UV-A or UV-B range, from 200-400 nanometers.

The surgical wrap damage detection system wherein the light source comprising a wavelength emission in substantially the UV-A or UV-B range, from 10-400 nanometers.

The surgical wrap damage detection system wherein the light source selectively absorbed by fluorescent dye are disrupted fiber edges, resulting in visible fluorescence at the fiber edge and circumferentially highlighting the damage.

These and other objects and advantages of the invention will be apparent from the following description, the accompanying drawings and the appended claims.

BRIEF DESCRIPTION OF THE ACCOMPANYING DRAWINGS

DETAILED DESCRIPTION OF THE PREFERRED EMBODIMENTS

Figure 1A:
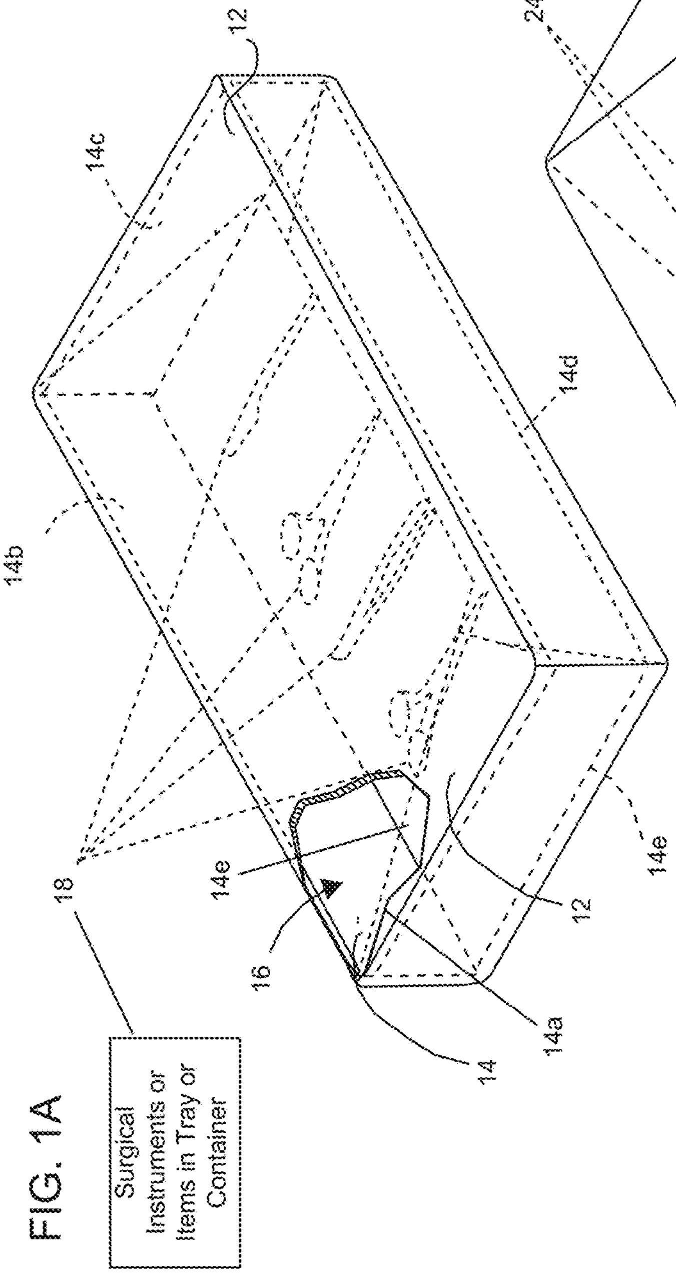
FIG. 1A is a perspective view of a surgical instrument wrap that wraps a surgical tray (shown in phantom) and that utilizes a diffusible fluorescent layer and a damage or indication means.

Referring now to FIGS. 1-9, a surgical instrument covering or wrap 12 and damage detection system and method 10 is shown. The wrap 12 and the damage detection system and method 10 provide a damage detection or damage indication means for the wrap 12 in the form of a heat-resistant and gas permeable fluorescent layer, which will not discolor surgical instrumentation and will be detectable under certain light wavelengths for operating room inspection. In general, and as described herein, the damage detection system and method 10 provides means and apparatus for detecting when the wrap 12 on a surgical instrument tray, box or container 14 has been damaged, such as in the form of tearing, puncture or other disruption to ensure or preserve the sterility of surgical instruments or items 18 in the surgical instrument tray, box or container 14 covered by the wrap 12. With this general background of understanding, various embodiments will now be described.

The damage detection system and method 10 comprises the wrap 12 that is situated on the surgical instrument tray, box or container 14. It should be understood that while the embodiment being described relates to a surgical tray, box or container and protection of surgical instruments or items 18 therein, it could be used with other trays having containers having items, such as non-surgical items, where it is desired to protect them from unwanted contamination area or debris. The surgical instrument tray, box or container 14 comprises a plurality of walls 14*a*, 14*b*, 14*c* and 14*d*, which are integral with or coupled to a bottom surface 14*e* and which define a receiving area 16 for receiving a plurality of items such as surgical instruments or items 18. The embodiment being described shows the wrap 12 being situated or wrapped around the tray, box or container 14 to protect surgical instruments or items 18 therein. Again, it should be understood that the wrap 12 may be used with other environments where it is necessary to protect items and to provide a damage indication system for use with other types of containers that contain items that need to, for example, remain sterile, undamaged, or where it is necessary to determine whether or not the wrap 12 around the tray, box or container 14 has been broken. It is important for security purposes of the surgical instruments or items 18 desired to detect whether or not the wrap 12 has been compromised, damaged, perhaps, inappropriately accessed or accessed by unauthorized personnel. The wrap 12 is especially suited for detecting or preserving the sterility or security of the surgical instruments or items 18 situated in the tray, box or container 14.

Figure 2:
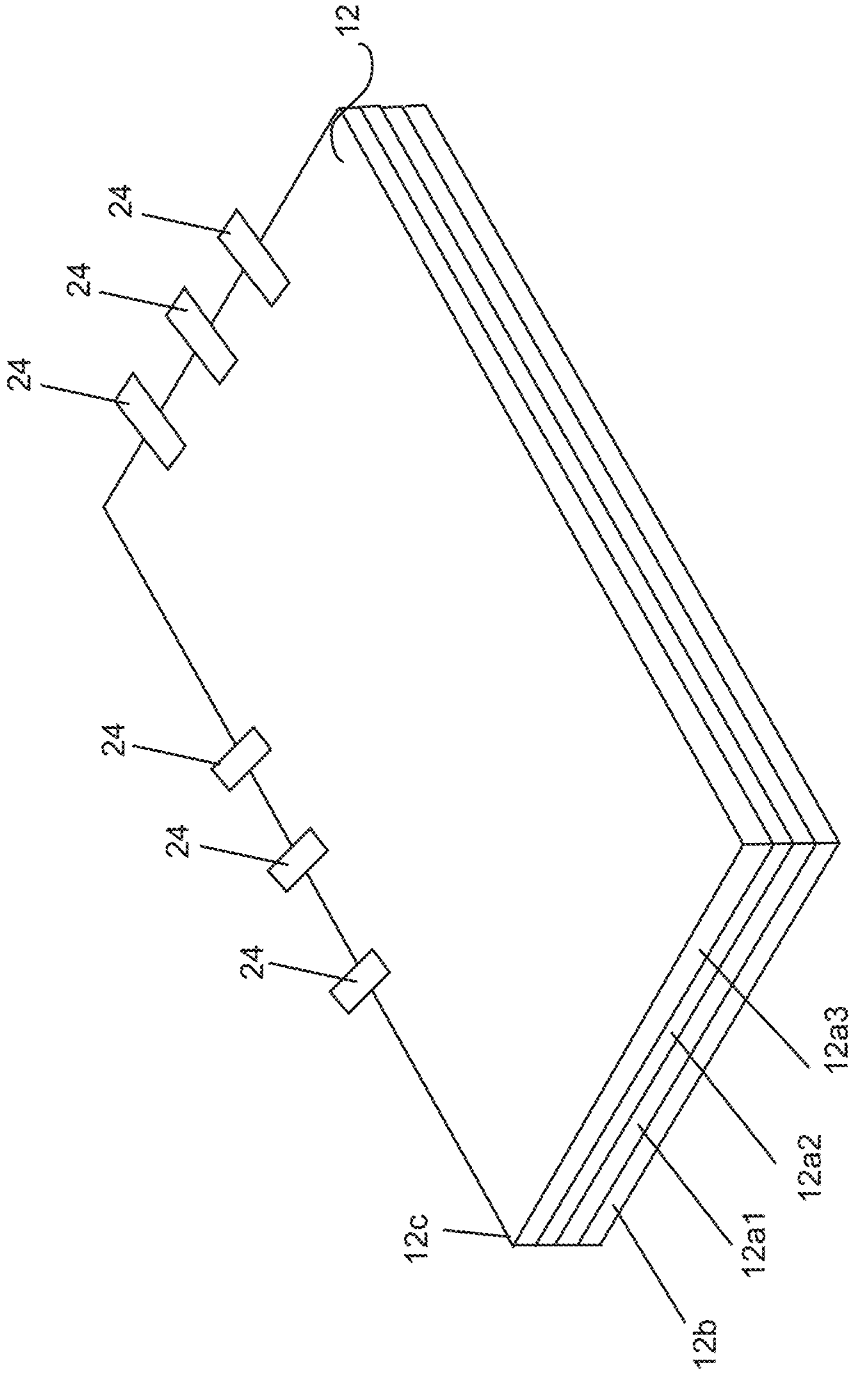
FIG. 2 is a plan view of the wrap illustrating the various fibrous layers and dye layer.
Figure 3:
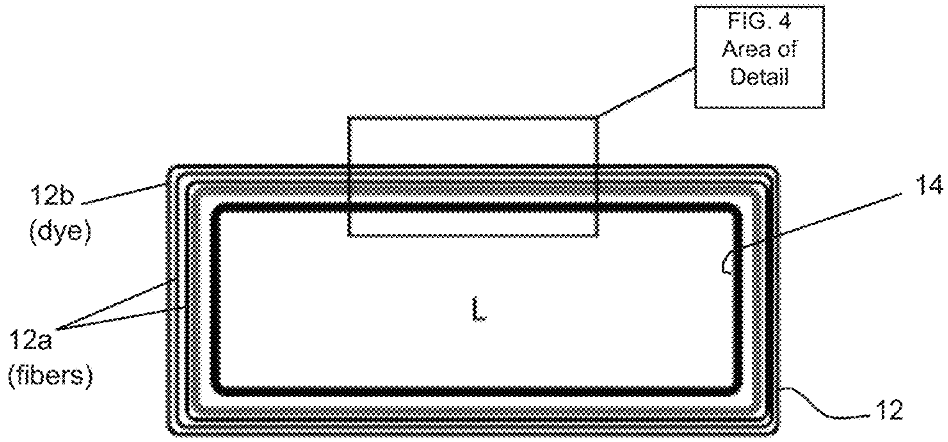
FIG. 3 is a plan view of the wrap surrounding the tray and showing the various layers of the wrap.
Figure 4:
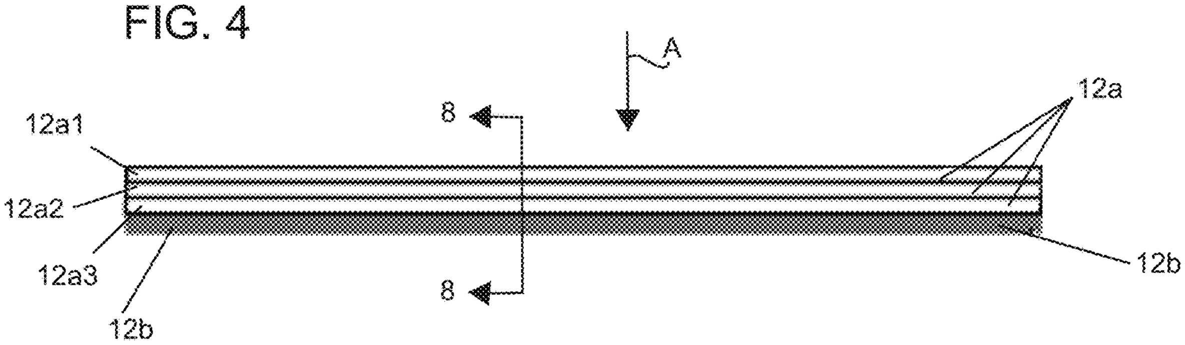
FIG. 4 is an exploded view of the details shown in FIG. 3 further illustrating the various fibrous layers and diffusible layer or dye layer.

Referring now to FIGS. 2-5, the wrap 12 comprises at least one fibrous layer 12*a* which will now be described relative to FIGS. 2-6. The wrap 12 is illustrated in FIGS. 2-4. For ease of understanding, the area of detail in FIG. 3 is exploded and enlarged as shown in FIG. 4. Notice in FIG. 4 that the wrap 12 comprises a multi-layer construction as illustrated in FIGS. 2-8. The construction comprises the at least one fibrous layer 12*a*. In the illustration being described, the at least one fibrous layer 12*a* may comprise a plurality of fibrous layers 12*a*1, 12*a*2 and 12*a*3 that comprise a predetermined arrangement and selection of fibers. In the illustration being described, the at least one fibrous layer 12*a* comprises a structure of cellulosic fibers, but it should be understood that the at least one fibrous layer 12*a* could be comprised of other types of fibers, such as polymer fibers, nylon, carbon fiber, or other types of non-cellulose fibers. In the illustration being described, the at least one fibrous layer 12*a* comprises a plurality of cellulose fibers that are organized and arranged in either a random or a predetermined pattern.

Figure 6:
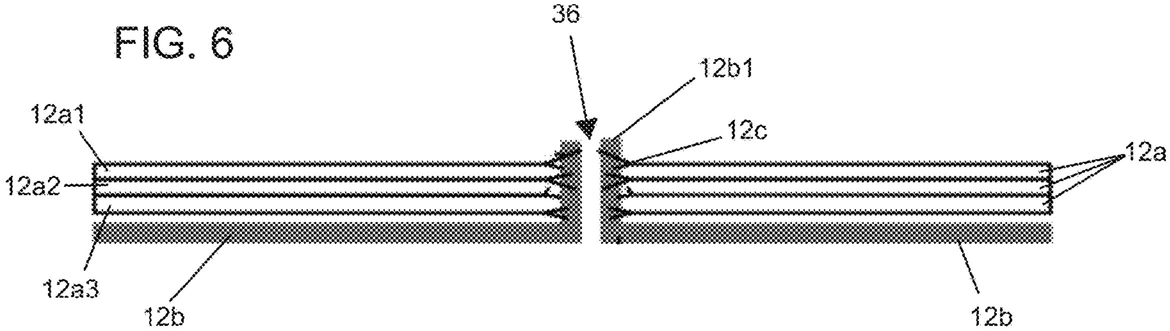
FIG. 6 is a view illustrating the at least one diffusible agent or dye diffusing or wicking into the disrupted or damaged edges of the cellulose fibers.
Figure 7:
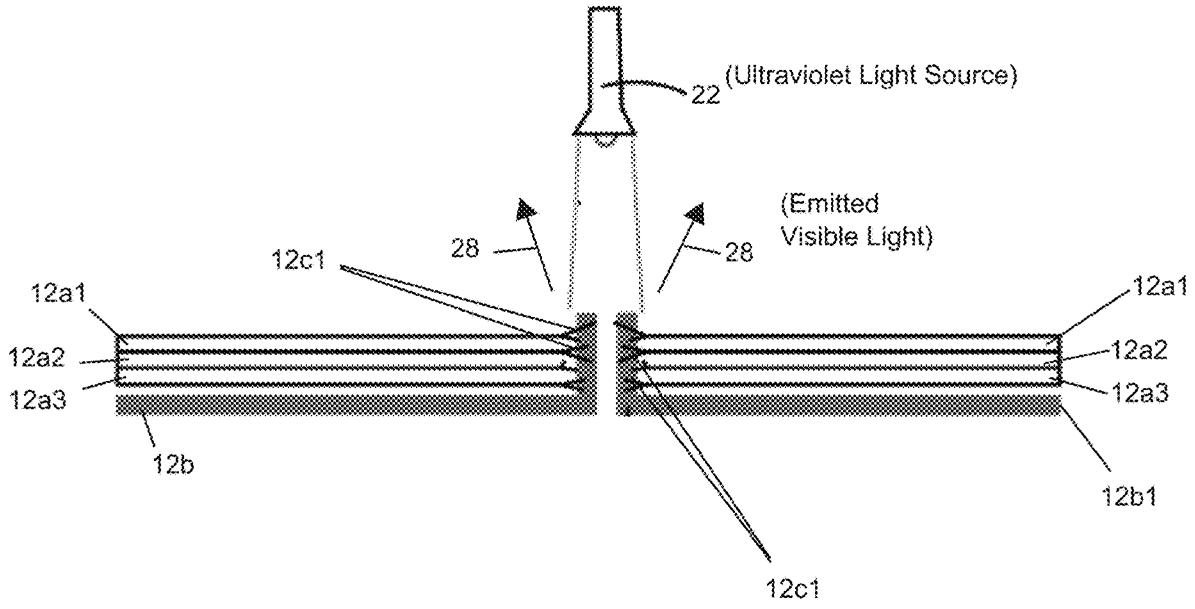
FIG. 7 is a view similar to FIG. 6 illustrating a light source, such as an ultraviolet light source, illuminating the dye so that it can generate an emissive wavelength in the visible spectrum.
Figure 8:
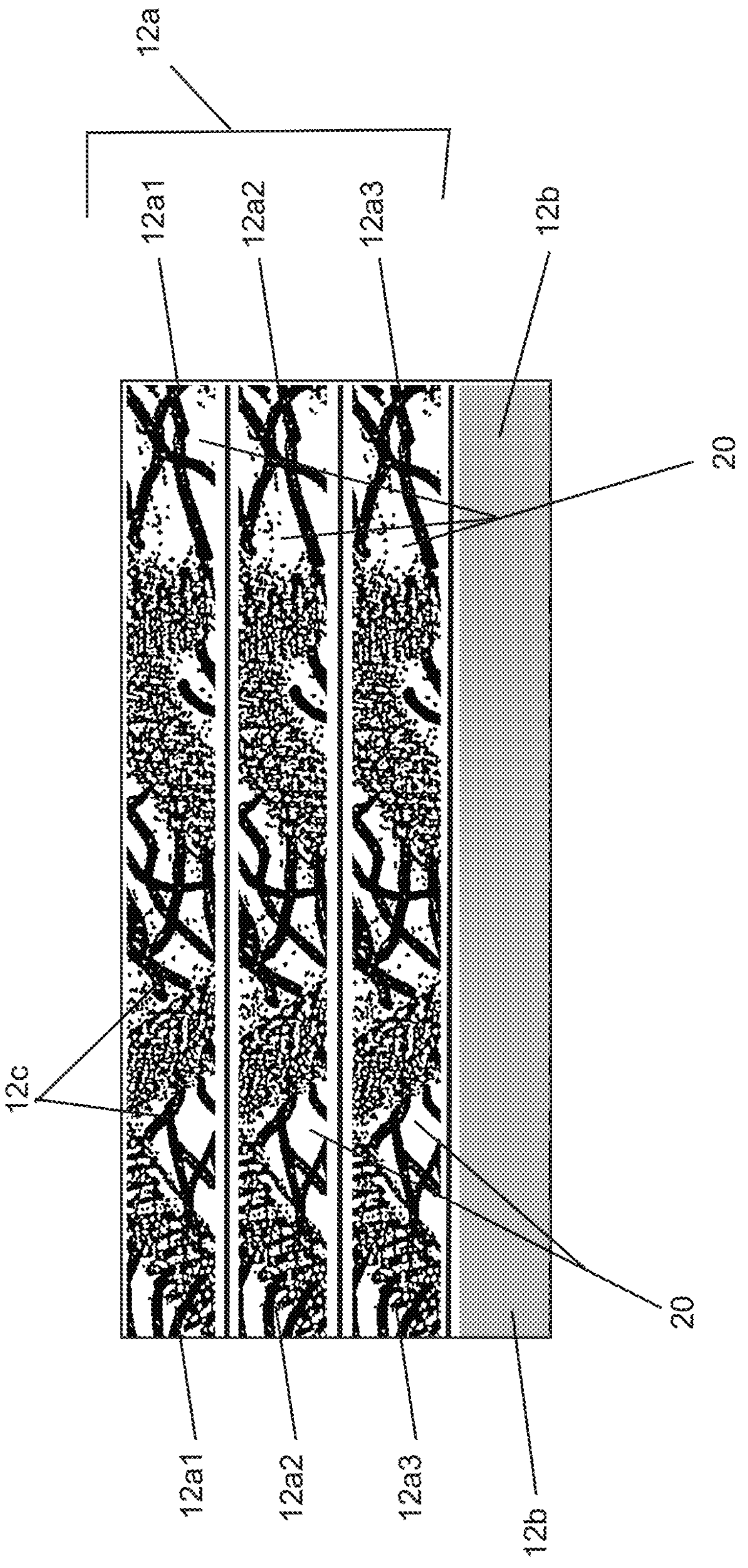
FIG. 8 is a view taken along the line 8-8 in FIG. 4 and further illustrating the various at least one fibrous layer and at least one diffusible agent or dye layer.

FIG. 8 is a sectional view taken along the line 8-8 in FIG. 4 which shows an illustrative arrangement of fibers in the various layers. In the illustration being described, the at least one fibrous layer 12*a* comprises the plurality of fibrous layers 12*a*1, 12*a*2 and 12*a*3, as illustrated in FIGS. 3-8. Notice in FIG. 8 that this illustration comprises the plurality of fibrous layers 12*a*1, 12*a*2 and 12*a*3 having a plurality of fibers 12*c* (FIG. 8) and in this embodiment the fibrous layers are cellulose fibrous layers. The plurality of fibers 12*c* may be arranged in either a predetermined or a random orientation to provide a matte or layer of fibers. It is important to understand that the plurality of fibrous layers 12*a*1, 12*a*2 and 12*a*3 comprise or define a plurality of voids or areas 20. It is important to understand that the organization and arrangement of the fibers and the voids or areas 20 define a permeable matte to permit, for example, steam to pass therethrough in order to sterilize the surgical instruments or items 18 inside the tray, box or container 14. Note in FIG. 8 that the plurality of fibers 12*c* create a cellulose matte or layer that permits steam to diffuse therethrough in order to sterilize the instruments 18, while preventing contamination to pass into the receiving area 16. The wrap 12 and various fibrous layers act as a filter to collect contamination.

The damage detection system and method 10 comprises the at least one diffusible agent or dye layer 12*b*, comprising a diffusible agent or dye 12*b*1 which fluoresces when exposed to a specific light wavelength or emission light 28 (FIG. 7). In the illustration being described, the at least one diffusible agent or dye layer 12*b* comprises the diffusible agent or dye 12*b*1 which fluoresces when exposed to a specific wavelength. The at least one diffusible agent or dye layer 12*b* comprises one or more reactive dyes, conjugated dyes and/or proteins with an absorption wavelength of 200-400 nanometers. It should be understood that the absorption wavelength range may preferably provide detection by ultraviolet, visual, infrared, or other areas of the electromagnetic spectrum. The range may be wide, such as 10-400 nanometers, medium (e.g., 200-400 nanometers) or narrow (300-400 nanometers). It should be understood that the at least one diffusible agent or dye layer 12*b* comprises an emission wavelength in the visible spectrum that facilitates enabling a person to view the at least one diffusible agent or dye 12*b*1 under, for example, a light source 22 (FIG. 7). The light source 22 may comprise a wavelength emission in substantially the UV-A or UV-B range, from 200-400 nanometers. The use of the light source 22 will be described later herein.

Figure 1B:
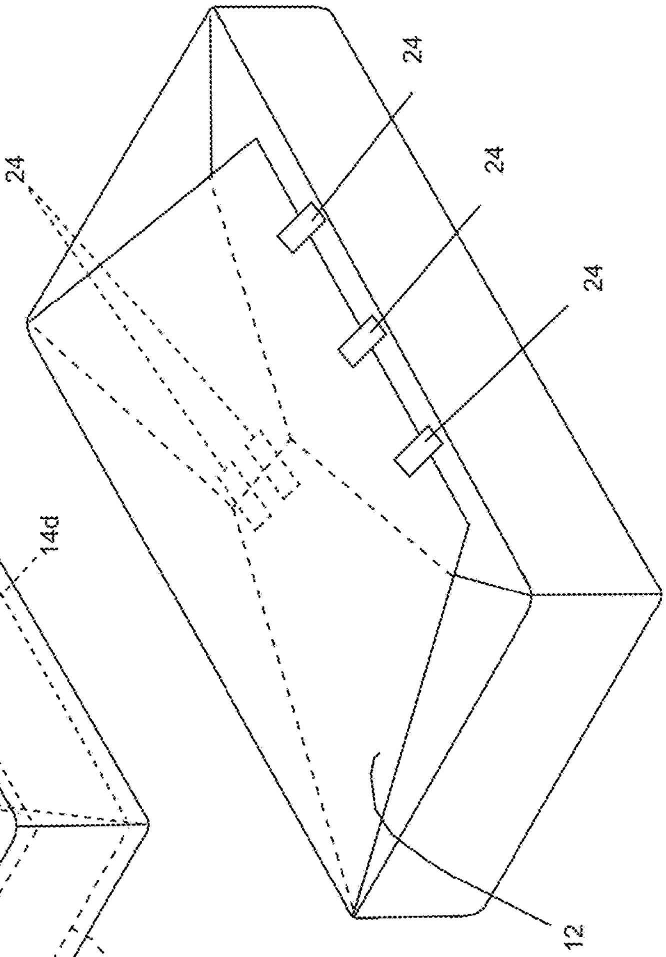
FIG. 1B is a bottom view of a wrapped surgical tray showing the wrap draped over the surgical tray and illustrating adhesive strips securing the wrap on the surgical tray.

As understood, note in FIG. 4 that at least one diffusible agent or dye layer 12*b* is situated underneath at least one of the plurality of fibrous layers 12*a*1-12*a*3, and initially it is not visible by the naked eye when viewing in the direction of arrow A in FIG. 4 because the at least one diffusible agent or dye layer 12*b* is shielded or hidden by the plurality of fibrous layers 12*a*1-12*a*3. It is important to understand that the at least one fibrous layer 12*a* provides a barrier layer comprising the structure of cellulose fibers illustrated in FIG. 8 and the barrier layer cooperates with the at least one diffusible agent or dye layer 12*b* which are disposed such that the disruption of any of the plurality of fibrous layers 12*a*1-12*a*3 or the surgical instruments or items 18 therein will result in the diffusible agent or dye 12*b*1 penetrating the plurality of fibrous layers 12*a*1-12*a*3. As illustrated in FIGS. 1A-1B, the wrap 12 is situated or draped around the tray, box or container 14 manually or mechanically with a machine and then secured thereon with a plurality with adhesive strips 24 (FIG. 2). It should be understood that other means for securing the wrap 12 may be provided, such as by using Velcro®, adhesive, or other types of fasteners or the like so that the wrap 12 envelops at least a portion of the tray, box or container 14. It is important to understand that the at least one fibrous layer 12*a* and the at least one diffusible agent or dye layer 12*b* are arranged on the tray, box or container 14 and the adhesive strips 24 are used to secure the wrap 12 on the tray, box or container 14. This is illustrated in the bottom view of FIG. 1B showing the wrap 12 being secured to the tray, box or container 14 after it is draped or arranged thereon.

Advantageously, the at least one fibrous layer 12*a* and the at least one diffusible agent or dye layer 12*b* are arranged on the tray, box or container 14 such that a disruption or damage to at least one of the fibers of the at least one fibrous layer 12*a* causes selective diffusion or wicking of at least a portion of the diffusible agent or dye into the disrupted or damaged at least one fibrous layer 12*a* so that at least a portion of the disrupted or damaged at least one fibrous layer 12*a* becomes colored, stained or dyed by the at least a portion of the at least one diffusible agent or dye layer 12*b*. After at least a portion of the disrupted or damaged at least one fibrous layer 12*a* has received the at least one diffusible agent or dye 12*b*1, it may fluoresce when exposed to the light source 22 (FIG. 7), which in the embodiment being described emits light at a predetermined wavelength. In the illustration being described, the light source 22 emits ultraviolet light. The light source 22 may be a portable light source or may be a lamp or other ultraviolet light source.

Figure 5:
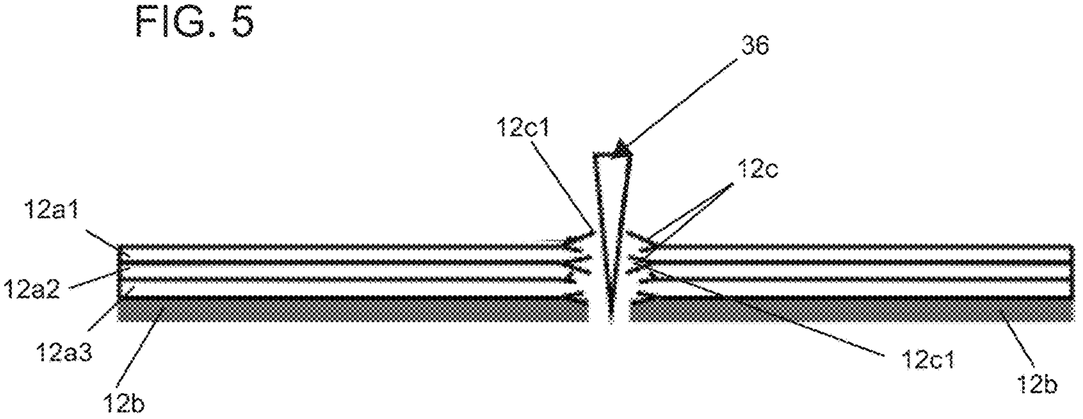
FIG. 5 is a view illustrating damage to the surgical wrap wherein an instrument disrupts or damages the cellulose fibers in the fibrous layers thereby exposing the porous edges of fibers.

It is important to understand that the damage detection system and method 10 provides a damage indicator or damage indication means for surgical wraps. Advantageously, the wrap 12 provides a gas permeable fluorescent layer using the at least one diffusible agent or dye layer 12*b*. In the illustration being described, the at least one diffusible agent or dye layer 12*b* is heat resistant and gas permeable. This permits, for example, the tray, box or container 14 and wrap 12 to be exposed to heat and steam sterilization which will penetrate the wrap 12 and sterilize the surgical instruments or items 18 therein, while still enabling damage detection as described herein. It is important to understand that the plurality of fibrous layers 12*a*1-12*a*3 remain substantially impervious, when intact, to penetration from the at least one diffusible agent or dye layer 12*b* in conditions of heat in excess of 100 degrees Celsius and relative humidity of greater than 50%. In one illustrative embodiment, the at least one fibrous layer 12*a* comprises a non-porous and/or closed-cell conformation, but which converts to a porous or open-cell conformation upon the introduction of a mechanical disruption or damage to one or more fibers 12*c* in at least one fibrous layer 12*a* (FIG. 8). Once the porous or open-cell or damage occurs, the at least one diffusible agent or dye layer 12*b* may diffuse or wick into the broken layers as illustrated in FIGS. 5-7. In this regard, FIG. 5 illustrates damage to the wrap 12 where an instrument or device disrupts or damages one or more of the plurality of fibers 12*c* which exposes their porous edges 12*c*1. It should be understood that the light source 22 may be selectively absorbed by fluorescent dye at disrupted fiber edges, resulting in visible fluorescence at the porous edges 12*c*1 (FIG. 6) and circumferentially highlighting the damage. Once the porous edges 12*c*1 are exposed, the at least one diffusible agent or dye layer 12*b* may diffuse or wick into the layers, such that the at least one diffusible agent or dye 12*b*1 moves upward (as viewed in FIG. 6) via the diffusion gradient towards the disruption edges of the plurality of fibers 12*c*. In general, the damage to the at least one fibrous layer 12*a* is not visible until exposed to the light source 22, whereupon the at least one diffusible agent or dye 12*b*1 becomes visible to the naked eye and thereby indicates to the user that damage has occurred and that the surgical instruments or items 18 in the tray, box or container 14 may be contaminated with unwanted debris, bacteria or the like as illustrated in FIG. 7.

In one embodiment, the at least one fibrous layer 12*a* comprises a discreet layer comprising a polymer, textile, fibrous, hydrogel, membrane, matrix or similar layer to a allow for localization, retention, and outward diffusion of the at least one diffusible agent or dye 12*b*1. The at least one diffusible agent or dye 12*b*1 may be mixed with a carrier, such as a mineral and/or water-proofing agent and thermal agent or carrier that is heat stable, not water soluble and that will not discolor the surgical instruments or items 18 yet will be detectable under the predetermined wavelengths of light from the light source 22. This is especially advantageous for an operating room inspection of a wrapped tray, box or container 14 to ensure that the surgical instruments or items 18 have not become contaminated. The inspection is quick and easy and merely requires that the tray, box or container 14 to be placed under the light source 22. If a disruption or damage, such as a penetration or break in the at least one fibrous layer 12*a* has occurred, then it can be presumed that the surgical instruments or items 18 therein may have been affected or contaminated. In response, the surgical instruments or items 18 therein are not used, for example, during a surgical procedure, thereby reducing or eliminating the chance of a person or patient becoming infected. The damage detection system and method 10, therefore, preserves the sterility of the equipment in the surgical procedures, while providing a convenient and easy means and apparatus for detecting contamination.

The disruption or damage to the at least one fibrous layer 12*a* may comprise at least one or a plurality of damaged fibers 12*c* that are torn, cut, ripped, shredded, damaged, altered to create voids or the like. In general, anything that disrupts the integrity or constitution of the plurality of fibers 12*c* that make up the at least one fibrous layer 12*a* will cause at least a portion of the any damaged fibers 12*c* to become colored, stained or dyed by at least a portion of the at least one diffusible agent or dye layer 12*b* which diffuses or wicks into the torn, cut, ripped, shredded, damaged area of the plurality of fibers 12*c*.

Figure 9:
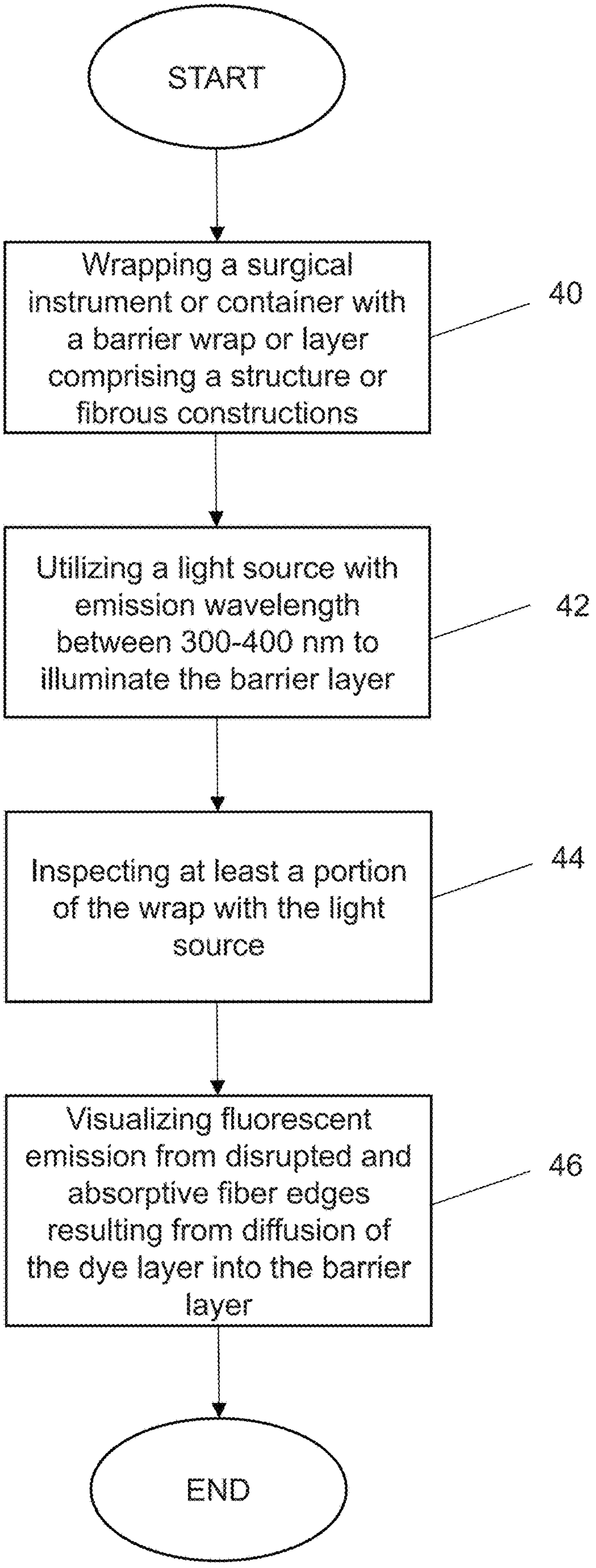
FIG. 9 is a schematic diagram of the steps of the method and process for locating damage to the surgical wrap.

Referring now to FIG. 9, the use of the damage detection system and method 10 for locating damage to the wrap 12 will now be described. The process begins at block 40 by wrapping the surgical instrument tray, box or container 14 with the wrap 12 that comprises the structure of fibers that make up the at least one fibrous layer 12*a*. The barrier layer defines the wrap 12 which also comprises the at least one diffusible agent or dye layer 12*b*, and it fluoresces when the wrap 12 is penetrated or damaged and exposed to a specific light wavelength, such as an ultraviolet wavelength, as described earlier herein. At block 42, a user utilizes the light source 22 with an emission wavelength between 200-400 nanometers to illuminate the barrier layer. The method or process continues to block 44 wherein inspecting at least a portion of the wrap 12 with the light source 22. The process then proceeds to block 46 wherein the user visualizes the wrap 12 and any fluorescent emission from the porous edges 12*c*1 that results from diffusion of the at least one agent or dye layer 12*b* into the at least one fibrous layer 12*a*. Notice that fluorescent emission is localized to the disrupted porous edges 12*c*1 resulting in circumferential fluorescence about the damaged or disrupted area 36 (FIGS. 5 and 6).

ADDITIONAL CONSIDERATIONS

1. It should be understood that the at least one fibrous layer 12*a* may comprise a plurality of fibrous layers, such as the plurality of fibrous layers 12_a_1-12_a_3 or may comprise a single fibrous layer. It is important to understand that the at least one fibrous layer 12_a_ overlays at least a portion of the diffusible agent or dye layer 12_b_ so that the diffusible agent or dye 12_b_1 is not visible by the naked eye until at least one fiber of the at least one fibrous layer 12_a_ is damaged or disrupted. Again, after the at least one diffusible agent or dye layer 12_b_ diffuses into the damaged or disrupted at least one fibrous layer 12_a_, the diffusible agent or dye 12_b_1 does not fluoresce and is not detectable to the naked eye until exposed to light from the light source 22 of the predetermined light wavelength mentioned earlier, which in the illustration being described is light in the ultraviolet wavelength. The agent or dye 12_b_1 has a predetermined viscosity or flow rate. As mentioned earlier, the at least one fibrous layer 12_a_ and the at least one agent or dye layer 12_b_ are heat resistant and gas permeable so that surgical instruments or items 18 in the tray, box or container 14 may be sterilized after the wrap 12 and the at least one diffusible agent or dye layer 12_b_ are situated on the tray, box or container 14, with the plurality of fibrous layers 12_a_1, 12_a_2, 12_a_3 remaining substantially intact.

2. In the illustration being described and as mentioned, the at least one fibrous layer 12_a_ comprises the plurality of cellulose fibers 12_c_ comprising at least one of a non-porous or closed-cell conformation that converts to a porous or open-cell conformation upon the disruption of one of the at least one fibrous layers 12_a_ so that disruption or damage facilitates diffusion of the at least one diffusible agent or dye layer 12_b_ into the damaged or disrupted portion of the at least one fibrous layer 12_a_ so that damage can be detected with the light source 22. Thus, the at least one fibrous layer 12_a_ is disposed such that the disruption increases one or more of fiber surface areas, such as the areas at the edges 12_c_1 (FIG. 5), fiber porosity or fiber open-cell conformation, thereby resulting in increased diffusion gradient between the disrupted fibers of the at least one fibrous layer 12_a_ and the fiber ends 12_c_1 and the diffusible agent or dye 12_b_1. As mentioned earlier, the diffusible agent or dye layer 12_b_ may comprise one or more reactive dyes, conjugated dyes and/or proteins with an absorption wavelength of 200-400 nanometers, and an emission wavelength in the visible spectrum.

3. The at least one fibrous layer 12_a_ remains substantially impervious, when intact, to penetration from the diffusible agent or dye 12_b_1 in conditions of heat in excess of 100 degrees C. and relative humidity greater than 50%.

4. The diffusible agent or dye 12_b_1 may be imported into the surface of the at least one fibrous layer 12_a_ or may comprise a discrete layer comprising a polymer, textile, fibrous, hydrogel, membrane, matrix, or similar layer to allow for localization, retention, and outward diffusion of the diffusible agent or dye 12_b_1.

5. It is important to note that the dye layer 12_b_ is the bottom most layer and is not visible until damage or disruption occurs to the at least one fibrous layer 12_a_. It will not fluoresce if exposed to the light source 22 because it is the bottom most layer. Once damage has occurred, dye 12_b_1 will diffuse and wick into the damaged fibers of the at least one fibrous layers 12_a_ and thereby provide means and ability to quickly and easily view the damage using the light source 22.

Advantageously, another embodiment of this invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A surgical tray damage protection system for use with a surgical instrument tray having at least one surgical instrument, said damage protection system comprising:

at least one fibrous layer comprising a predetermined arrangement of fibers; and at least one diffusible agent layer comprising a diffusible agent which fluoresces when exposed to a light having a predetermined light wavelength;

said at least one fibrous layer and said at least one diffusible agent layer being arranged on said surgical instrument tray such that upon a disruption or damage to at least one fiber of said at least one fibrous layer, at least a portion of said at least one diffusible agent layer diffuses into said disrupted or damaged at least one fiber so that at least a portion of said disrupted or damaged at least fiber becomes colored, stained or dyed by said at least a portion of said at least one diffusible agent layer;

said at least a portion of said disrupted or damage at least one fiber having said agent fluorescing when exposed to light of a predetermined wavelength.

2. The surgical tray damage protection system as recited in claim 1 wherein said at least one fibrous layer comprises a plurality of cellulose fibers.

3. The surgical tray damage protection system as recited in claim 1 wherein said agent comprises an absorption wavelength of 300-400 nanometers and an emission wavelength in the visible spectrum.

4. The surgical tray damage protection system as recited in claim 1 wherein said agent comprises an absorption wavelength of 200-400 nanometers and an emission wavelength in the visible spectrum.

5. The surgical tray damage protection system as recited in claim 1 wherein said agent comprises an absorption wavelength of 10-400 nanometers and an emission wavelength in the visible spectrum.

6. The surgical tray damage protection system as recited in claim 1 wherein said diffusible agent comprises a diffusible dye that is a fluid having a predetermined viscosity and flow rate.

7. The surgical tray damage protection system as recited in claim 1 wherein at least one fibrous layer is at least one of gas permeable or heat resistant so that instruments in said surgical tray may be sterilized after said at least one fibrous layer and said diffusible agent layer are situated on said surgical tray, with said layers remaining substantially intact.

8. The surgical tray damage protection system as recited in claim 1 wherein at least one fibrous layer comprises a plurality of cellulose fibers comprising at least one of a non-porous or closed-cell conformation that converts to a porous or open-cell conformation upon said disruption or damage to facilitate diffusion of said agent into said damage or disrupted portion of said at least one fiber.

9. The surgical tray damage protection system as recited in claim 1 wherein said at least one fibrous layer, upon mechanical disruption increases one or more of fiber surface area, fiber porosity or fiber open-cell conformation, resulting in increased diffusion gradient between said disrupted fibers and said diffusible agent.

10. The surgical tray damage protection system as recited in claim 1 where said diffusible agent comprises one or more reactive dyes, conjugated dyes and/or proteins with an absorption wavelength of 300-400 nanometers, and an emission wavelength in the visible spectrum.

11. The surgical tray damage protection system as recited in claim 1 where said diffusible agent comprises one or more reactive dyes, conjugated dyes and/or proteins with an absorption wavelength of 200-400 nanometers, and an emission wavelength in the visible spectrum.

12. The surgical tray damage protection system as recited in claim 1 where said diffusible agent comprises one or more reactive dyes, conjugated dyes and/or proteins with an absorption wavelength of 10-400 nanometers, and an emission wavelength in the visible spectrum.

13. The surgical tray damage protection system as recited in claim 1 wherein said at least one fibrous layer remains substantially impervious, when intact, to penetration from said diffusible agent in conditions of heat in excess of 100 degrees C. and relative humidity greater than 50%.

14. The surgical tray damage protection system as recited in claim 1 wherein said diffusible agent imported into the surface of said at least one fibrous layer or comprising a discrete layer;

said discrete layer comprising a polymer, textile, fibrous, hydrogel, membrane, matrix, or similar layer to allow for localization, retention, and outward diffusion of said dye.

15. The surgical tray damage protection system as recited in claim 1 wherein said agent comprises at least one of a fluorescent dye, a reactive dye, a conjugated dye or a protein.

16. The surgical tray damage protection system as recited in claim 15 wherein said agent comprises an absorption wavelength of 300-400 nanometers and an emission wavelength in the visible spectrum.

17. The surgical tray damage protection system as recited in claim 15 wherein said agent comprises an absorption wavelength of 200-400 nanometers and an emission wavelength in the visible spectrum.

18. The surgical tray damage protection system as recited in claim 15 wherein said agent comprises an absorption wavelength of 10-400 nanometers and an emission wavelength in the visible spectrum.

19. The surgical tray damage protection system as recited in claim 1 wherein said disruption or damage to at least one fiber of said at least one fibrous layer comprises a plurality of damaged fibers that are torn, cut, ripped, shredded, damaged or the like that disrupts the integrity or constitution of said plurality of fibers in said fibrous layer, at least a portion of said plurality of damaged fibers becoming colored, stained or dyed by said at least a portion of said at least one diffusible agent layer which diffuses into said disrupted, torn, ripped, shredded or damaged areas of said plurality of fibers.

20. The surgical tray damage protection system as recited in claim 19 wherein said agent comprises at least one of a fluorescent dye, a reactive dye, a conjugated dye or a protein, said damage to said at least one fiber comprises a damaged to said at least one fibrous layer comprising a plurality of torn edges of said fibers that absorb said agent.

21. The surgical tray damage protection system as recited in claim 1 wherein said at least one fibrous layer overlays a majority of said at least one diffusible agent so that said agent is not visible until at least one fiber of said at least one fibrous layer is damaged or disrupted.

22. The surgical tray damage protection system as recited in claim 21 wherein after said at least one diffusible agent diffuses into said damaged or disrupted plurality of fibers, said diffusible agent does not fluoresce and is not detectible to the naked eye until exposed to said predetermined light wavelength.

23. A container having a damage indication wrap at least partially covering said container, said container being adapted to house at least one item thereon, said container comprising:

a container body having an area therein for receiving said at least one item; the damage indication wrap comprising:

at least one fibrous layer comprising a predetermined arrangement of fibers; and at least one diffusible agent layer comprising a diffusible agent which fluoresces when exposed to a light having a predetermined light wavelength;

said at least one fibrous layer and said at least one diffusible agent layer being arranged on said container such that upon a disruption or damage to at least one fiber of said at least one fibrous layer, at least a portion of said at least one diffusible agent layer diffuses into said disrupted or damaged at least one fiber so that at least a portion of said disrupted or damaged at least fiber becomes colored, stained or dyed by said at least a portion of said at least one diffusible agent layer;

said at least a portion of said disrupted or damaged at least one fiber having said agent fluorescing when exposed to light of a predetermined wavelength.

24. The container having a damage indication wrap as recited in claim 23 wherein said container is a surgical tray and said at least one item is a surgical instrument.

25. The container having a damage indication wrap as recited in claim 23 wherein said at least one fibrous layer comprises a plurality of cellulose fibers.

26. The container having a damage indication wrap as recited in claim 23 wherein said agent comprises at least one of a fluorescent dye, a reactive dye, a conjugated dye or a protein.

27. The container having a damage indication wrap as recited in claim 23 wherein said agent comprises an absorption wavelength of 200-400 nanometers and an emission wavelength in the visible spectrum.

28. The container having a damage indication wrap as recited in claim 23 wherein said agent comprises an absorption wavelength of 10-400 nanometers and an emission wavelength in the visible spectrum.

29. The container having a damage indication wrap as recited in claim 23 wherein said diffusible agent comprises a diffusible dye that is a fluid having a predetermined viscosity and flow rate.

30. The container having a damage indication wrap as recited in claim 23 wherein at least one fibrous layer is at least one of gas permeable or heat resistant so that instruments in said container may be sterilized after said at least one fibrous layer and said diffusible agent layer are situated on said container, with said layers remaining substantially intact.

31. The container having a damage indication wrap as recited in claim 23 wherein at least one fibrous layer comprises a plurality of cellulose fibers comprising at least one of a non-porous or closed-cell conformation that converts to a porous or open-cell conformation upon said disruption or damage to facilitate diffusion of said agent into said damage or disrupted portion of said at least one fiber.

32. The container having a damage indication wrap as recited in claim 23 wherein said agent comprises an absorption wavelength of 300-400 nanometers and an emission wavelength in the visible spectrum.

33. The container having a damage indication wrap as recited in claim 32 wherein said agent comprises an absorption wavelength of 300-400 nanometers and an emission wavelength in the visible spectrum.

34. The container having a damage indication wrap as recited in claim 32 wherein said agent comprises an absorption wavelength of 200-400 nanometers and an emission wavelength in the visible spectrum.

35. The container having a damage indication wrap as recited in claim 32 wherein said agent comprises an absorption wavelength of 10-400 nanometers and an emission wavelength in the visible spectrum.

36. The container having a damage indication wrap as recited in claim 23 wherein said disruption or damage to at least one fiber of said at least one fibrous layer comprises a plurality of damaged fibers that are torn, cut, ripped, shredded, damaged or the like that disrupts the integrity or constitution of said plurality of fibers in said fibrous layer, at least a portion of said plurality of damaged fibers becoming colored, stained or dyed by said at least a portion of said at least one diffusible agent layer which diffuses into said disrupted, torn, ripped, shredded or damaged areas of said plurality of fibers.

37. The container having a damage indication wrap as recited in claim 36 wherein said agent comprises at least one of a fluorescent dye, a reactive dye, a conjugated dye or a protein, said damage to said at least one fiber comprises a damaged to said at least one fibrous layer comprising a plurality of torn edges of said fibers that absorb said agent.

38. The container having a damage indication wrap as recited in claim 23 wherein said at least one fibrous layer overlays a majority of said at least one diffusible agent so that said agent is not visible until at least one fiber of said at least one fibrous layer is damaged or disrupted.

39. The container having a damage indication wrap as recited in claim 38 wherein after said at least one diffusible agent diffuses into said damaged or disrupted plurality of fibers, said diffusible agent does not fluoresce and is not detectible to the naked eye until exposed to said predetermined light wavelength.

40. A surgical wrap comprising of:
- at least one fibrous barrier layer comprising a structure of cellulosic fibers;
- a diffusible dye layer comprising a diffusible dye which fluoresces when exposed to a specific light wavelength;
- said barrier layer and said dye layer disposed such that disruption of said fibers results in selective diffusion of said dye into said disrupted fiber edges;
- said disrupted fiber edges fluorescing when exposed to said light wavelength.

41. The surgical wrap as recited in claim 40 wherein said cellulosic fibers, upon mechanical disruption increases one or more of fiber surface area, fiber porosity or fiber open-cell conformation, resulting in increased diffusion gradient between said disrupted fibers and said fluorescent dye.

42. The surgical wrap as recited in claim 40 where said fluorescent dye comprises one or more reactive dyes, conjugated dyes and/or proteins with an absorption wavelength of 300-400 nanometers, and an emission wavelength in the visible spectrum.

43. The surgical wrap as recited in claim 40 where said fluorescent dye comprises one or more reactive dyes, conjugated dyes and/or proteins with an absorption wavelength of 200-400 nanometers, and an emission wavelength in the visible spectrum.

44. The surgical wrap as recited in claim 40 where said fluorescent dye comprises one or more reactive dyes, conjugated dyes and/or proteins with an absorption wavelength of 10-400 nanometers, and an emission wavelength in the visible spectrum.

45. The surgical wrap as recited in claim 40 wherein said cellulosic fibers remain substantially impervious, when intact, to penetration from said fluorescent dye in conditions of heat in excess of 100 degrees Celsius and relative humidity greater than 50%.

46. The surgical wrap as recited in claim 40 wherein said cellulosic fibers comprising a nonporous and/or closed-cell conformation, converting to porous and or open-cell conformation upon the event of mechanical disruption.

47. The surgical wrap as recited in claim 40 wherein said fluorescent dye imported into the surface of said fibrous barrier layer or comprising a discrete layer;
- said discrete layer comprising a polymer, textile, fibrous, hydrogel, membrane, matrix, or similar layer to allow for localization, retention, and outward diffusion of said dye.

48. A surgical wrap damage detection system comprising of:
- a barrier layer comprising a structure of fibrous construction;
- a diffusible dye layer which fluoresces when exposed to a specific light wavelength;
- said barrier layer and said dye layer disposed such that disruption of said fibers results in selective diffusion of said dye into said disrupted fiber edges;
- a light source emitting a wavelength equivalent to the absorption wavelength of said dye layer.

49. The surgical wrap damage detection system of claim 48 wherein said light source comprising a wavelength emission in substantially the UV-A or UV-B range, from 200-400 nanometers.

50. The surgical wrap damage detection system of claim 48 wherein said light source selectively absorbed by fluorescent dye are disrupted fiber edges, resulting in visible fluorescence at said fiber edge and circumferentially highlighting said damage.

51. A method for locating damage to a surgical wrap comprising:
- wrapping a surgical instrument or container with barrier layer comprising a structure of fibrous construction;
- said wrap further comprising a diffusible dye layer which fluoresces when exposed to a specific light wavelength;
- utilizing a light source with emission wavelength with an ultraviolet, visual, infrared or electromagnetic wavelength adapted to illuminate the barrier layer;
- visualizing fluorescent emission from disrupted and absorptive fiber edges resulting from diffusion of said dye layer into said barrier layer;
- said fluorescent emission localized to disrupted fiber edges resulting in circumferential fluorescence about said damage.

* * * * *